United States Patent [19]

Gutierrez et al.

[11] Patent Number: 5,688,996

[45] Date of Patent: Nov. 18, 1997

[54] ETHYENE CONTAINING CYSTEATE SEQUESTRANTS AND METHODS OF MANUFACTURE

[75] Inventors: Eddie Nelson Gutierrez, Midland Park; Shang-Ren Wu, Mahwah; Robert Charles Vermeer, Nutley, all of N.J.

[73] Assignee: Lever Brothers Company, Division of Conopco, Inc., New York, N.Y.

[21] Appl. No.: 618,218

[22] Filed: Mar. 19, 1996

[51] Int. Cl.[6] .................. C07C 309/08; C07C 309/13
[52] U.S. Cl. ............................................ 562/106
[58] Field of Search ................................. 562/106

[56] References Cited

U.S. PATENT DOCUMENTS 3,957,775  5/1976  Lamberti .................. 260/247.1 E
5,472,642  12/1995  Gutierrez et al. ................ 252/545

*Primary Examiner*—Joseph Conrad
*Attorney, Agent, or Firm*—James J. Farrell

[57] ABSTRACT

Novel compounds useful as sequestrants as well as builders for detergent compositions and methods for their preparation are disclosed.

20 Claims, No Drawings

ETHYENE CONTAINING CYSTEATE SEQUESTRANTS AND METHODS OF MANUFACTURE

FIELD OF THE INVENTION

The present invention relates to improved sequestrants and their use in detergent compositions. Specifically, it relates to improved cysteate sequestrants and laundry detergent compositions containing them. More specifically, it relates to ethylene aspartate cysteate acid, a novel non-phosphorous chelant, which assists in the removal of food, beverage and certain other organic stains from fabrics during the laundry process. Ethylene aspartate cysteate (EAC) can be used as a replacement for all or part of the chelants currently used in many existing laundry products, thereby yielding detergent formulations having reduced phosphorus content. The difficulties with phosphorus-containing compositions are well-documented.

Accordingly, it is highly desirable to be able to formulate detergent compositions with reduced levels of phosphorous-containing components which are potentially biodegradable, but still exhibit excellent cleaning and stain removal performance.

In addition, while the use of chelants in detergent compositions is generally desirable for enhanced stain removal, there is usually an efficacy/biodegradability trade-off with chelants and sequestrants. For example, chelants that provide the best stain removal tend to be totally non-biodegradable, while those that exhibit some level of biodegradability are poor in terms of stain removal.

It is an object of the present invention to provide a novel non-phosphorous biodegradable chelant for use in laundry detergent compositions.

It is another object of the present invention to provide improved laundry detergent compositions which exhibit excellent stain removal characteristics. It is a final object of the present invention to provide a novel effective chelant/sequestrant useful in detergent, personal product, cosmetic, food, oral hygiene, pharmaceutical and industrial compositions.

These and other objects of the invention will become readily apparent from the detailed description that follows.

BACKGROUND OF THE INVENTION

The use of aminopolycarboxylates as builders and laundry detergent additives is generally disclosed in the art. For example, U.S. Pat. No. 4,560,492 discloses laundry detergent compositions, essentially free of phosphate detergency builders, containing an aluminosilicate or organic detergency builder and from about 0.5% to about 10% by weight of the chelant, HEDTA.

U.S. Pat. No. 4,397,776 discloses liquid laundry detergent compositions having chelating agents which include aminopolycarboxylates such as NTA, EDTA, DTPA and HEDTA.

U.S. Pat. No. 3,920,564 discloses softener/detergent formulations containing surfactants, quaternary ammonium or diamine fabric softeners, and a builder salt selected from aminopolycarboxylates and/or sodium citrate. Examples of suitable aminopolycarboxylates include NTA, EDTA and HEDTA.

U.S. Pat. No. 3,151,084 discloses detergent compositions in which solubility is said to be improved by the addition of 0.25% to 4% of a mixture of EDTA and a solubilizing agent selected from salts of N,N-di(2-hydroxyethyl) glycine, iminodiacetic acid, NTA and HEDTA.

U.S. Pat. No. 4,704,233 discloses ethylenediamine N,N'-disuccinic acid and salts as a detergent additive which is said to enhance the removal of food and beverage stains.

U.S. Pat. No. 5,183,590 discloses N-(hydroxysuccinyl) cysteic acid as a corrosion inhibitor for aqueous systems.

None of these references disclose or recognize the compositions of the present invention or the unique ability of EAC to assist in the removal of stain from fabric.

In addition, none of these references disclose or recognize EAC is a novel potentially readily biodegradable chelant/sequestrant suitable for detergent, personal product, cosmetic, food, oral hygiene, pharmaceutical and industrial applications.

SUMMARY OF THE INVENTION

One embodiment of the invention specifically relates to laundry detergent compositions comprising:
 (a) from about 1% to about 75% by weight of a detergent surfactant selected from the group consisting of anionic surfactants, nonionic surfactants, zwitterionic surfactants, ampholytic surfactants, cationic surfactants, and mixtures thereof;
 (b) from about 0% to about 80% by weight of a detergency builder; and
 (c) from about 0.1% to about 50% by weight of ethylene aspartic cysteic acid or the alkali metal, alkaline earth, ammonium or substituted ammonium salts thereof, as well as mixtures thereof; and
 (d) the remainder is water and additional optional detersive ingredients.

The second embodiment of the invention relates to a novel non* phosphorous potentially readily biodegradable chelant suitable for detergent, personal product, oral hygiene, cosmetic, food, pharmaceutical and industrial applications. The novel chelant is known as ethylene aspartate cysteate, abbreviated as EAC.

DETAILED DESCRIPTION OF THE INVENTION

A. The Detergent Surfactant System

The amount of detergent surfactant included in the detergent compositions of the present invention can vary from about 1% to about 75% by weight of the composition depending upon the particular surfactant(s) used, the type of composition to be formulated (e.g., granular, liquid or concentrate) and the effects desired. Preferably, the detergent surfactant(s) comprises from about 5% to about 60% by weight of the composition. The detergent surfactant can be nonionic, anionic, ampholytic, zwitterionic or cationic. Mixtures of these surfactants can also be used.

B. Detergent Builders

Detergent compositions of the present invention contain inorganic and/or organic detergent builders to assist in mineral hardness control. These builders comprise from about 0% to about 80% by weight of the compositions. Built liquid formulations preferably comprise from about 0% to about 30% by weight of detergent builder, while built granular formulations preferably comprise from about 10% to about 50% by weight of detergent builder.

Suitable detergent builders include crystalline aluminosilicate ion exchange materials having the formula:

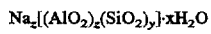

wherein z and y are at least about 6, the mol ratio of z to y is from about 1.0 to about 0.5; and x is from about 10 to about 264. Amorphous hydrated aluminosilicate materials useful herein have the empirical formula:

$$M_z(ZAlO_2 \cdot ySiO_2)$$

wherein M is sodium, potassium, ammonium or substituted ammonium, z is from about 0.5 to about 2, and y is 1; this material has a magnesium ion exchange capacity of at least about 50 milligram equivalents of $CaCO_3$ hardness per gram of anhydrous aluminosilicate.

Aluminosilicate ion exchange materials useful herein are commercially available. These aluminosilicates can be crystalline or amorphous in structure and can be naturally-occurring or synthetically derived. A method for producing aluminosilicate ion exchange materials is disclosed in U.S. Pat. No. 3,985,669, Krummel et al, issued Oct. 12, 1976, incorporated herein by reference. Preferred synthetic crystalline aluminosilicate ion exchange materials useful herein are available under the designations Zeolite A, Zeolite P (B), and Zeolite X. In an especially preferred embodiment, the crystalline aluminosilicate ion exchange material has the formula:

$$Na_{12}[(AlO_2)_{12}(SiO_2)_{12}] \cdot xH_2O$$

wherein x is from about 20 to about 30, especially about 27.

Other detergency builders useful in the present invention include the alkali metal silicates, alkali metal carbonates, phosphates, polyphosphates, phosphonates, polyphosphonic acids, $C_8$–$C_8$ alkyl monocarboxylic acids, polycarboxylic acids, alkali metal ammonium or substituted ammonium salts thereof and mixtures thereof. Preferred are the alkali metal salts of the above, especially sodium.

Useful water-soluble, nonphosphorous organic builders include the various alkali metal, ammonium and substituted ammonium polyacetates, carboxylates, polycarboxylates and polyhydroxysulfonates. Examples of polyacetate and polycarboxylate builders are the sodium, potassium, lithium, ammonium and substituted ammonium salts of ethylenediamine tetraacetic acid, ethylenediamine disuccinic acid (EDDS), nitrilotriacetic acid (NTA), oxydisuccinic acid (ODS), mellitic acid, carboxymethyloxysuccinic acid, (CMOS), benzene polycarboxylic acids and citric acid. For purposes of defining the invention, the organic detergent builder component which may be used herein does not include EAC or its salts, although EAC can be used as a builder as well as a chelant/sequestrant if desired.

C. Ethylene Aspartate Cysteate Acid (EAC) or Salts Thereof as well as Related Derivatives The compositions of the invention contain, as an essential component, from about 0.1% to about 50%, preferably from about 0.2% to about 15%, more preferably from about 0.3% to about 10%, of ethylene aspartic cysteic acid (EAC) or the alkali metal, alkaline earth metal, ammonium or substituted ammonium salts thereof, or mixtures thereof. Preferred EAC compounds for granular detergent compositions are the free acid and the corresponding sodium salt forms as well as mixtures thereof. Examples of such preferred sodium salts of EAC include NaEAC, $Na_2$ EAC, $Na_3$ EAC and $Na_4$ EAC, wherein Na is sodium. Preferred EAC compounds for liquid detergent compositions are the free acid and the corresponding substituted ammonium or potassium salt forms thereof. Examples of such preferred salts of EAC include (MEA) EAC, $(MEA)_2$ EAC, $(MEA)_3$ EAC, $(MEA)_4$ EAC, (TEA) EAC, $(TEA)_2$ EAC, $(TEA)_3$ EAC, $(TEA)_4$ EAC, $(DEA)_4$ EAC, $(K)_4$ EAC EAC and the like, wherein MEA is monoethanolamine, DEA is diethanolamine, TEA is triethanolamine and K is potassium.

The structure of the acid form of EAC is as follows:

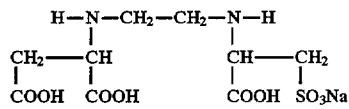

The structure of the sodium salt form of EAC is as follows:

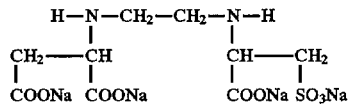

The structure of MEA form of EAC is as follows:

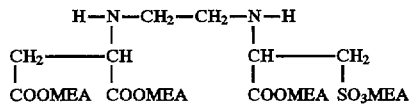

wherein MEA is monoethanolamine represented as $^+NH_3CH_2CH_2OH$.

The chelant/sequestrant of the invention, EAC, can be prepared from readily available fairly inexpensive raw materials such as cysteic acid (3-sulfoalanine or 0α-amino-β-sulfopropionic acid), aspartic acid and 1,2-dibromoethane (ethylenedibromide) as follows:

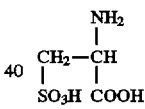

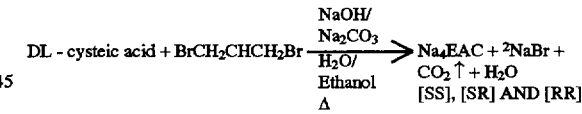

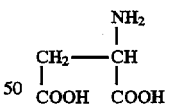

DL - aspartic acid

Cysteic acid can be prepared from cysteine or from cystine by oxidation with bromine in water. Cysteine is prepared from the hydrolysis of proteins and cystine is formed by air oxidation in alkaline water solutions of cysteine.

The synthesis of EAC from DL-cysteic acid and DL-aspartic acid yields a mixture of three optical isomers, namely; [SS], [SR] and [RR]. This is due to the presence of two asymmetric carbon atoms. Also, it is known that the biodegradation of certain amino polycarboxylates appears to be optical isomer-specific, with the [SS] isomer degrading most rapidly and extensively followed by the [SR] isomer and the [RR] isomer. Without being bound by theory, it is generally believed that the (SS) isomer of EAC degrades most quickly and readily.

The [S,S] isomer of EAC can be prepared from L-cysteic acid monohydrate, L-aspartic acid and 1,2-dibromoethane as follows:

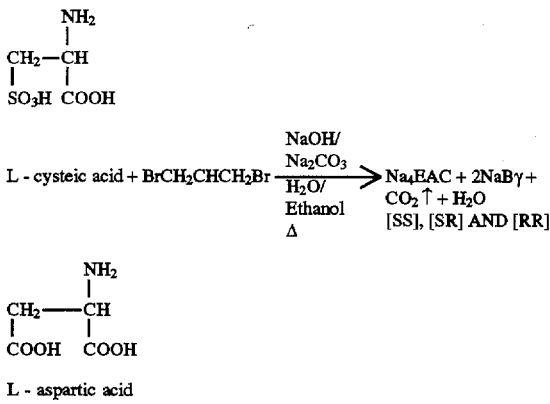

The chelant/sequestrant, EAC, possess excellent stain removal characteristics, especially on polyphenolic stains such as tea, coffee, blueberry, morello juice, strawberry and the like. EAC was found to provide stain removal performance equivalent to, or superior to . . . 1, 2 and 3 nitrogen containing polycarboxylates such as NTA, EDTA and DETPA which are currently used in many existing laundry products. By using EAC as a replacement for such chelants, it is now possible to formulate detergent compositions which contain reduced levels of phosphorous-containing components while still exhibiting excellent cleaning and stain removal characteristics.

Without being bound by theory, it is believed that ethylene aspartic cysteic acid and its salts, which are contained in the compositions of the present invention, act to chelate metal ions such as iron, manganese, zinc, copper, etc. which are constituents of certain organic stains. This, in turn, makes the stains easier to remove from the fabrics. It is also believed that such metal ions, which are always present in various amounts in wash liquors from pipes, environment, detergent ingredients, washing machines, dyes, soils, etc., have a detrimental effect on soils and stains, particularly on polyphenolic stains, such as wine, tea, grape juice, blueberry juice, coffee and the like, making such stains darker and more difficult to remove. The presence of EAC, however, acts to chelate such metal ions in the wash liquor enabling detergent materials to function more effectively and preventing stain metal interactions resulting in improved performance and cleaning. It is further believed that EAC can act to stabilize stains in the wash solution. Whatever the mechanism may be, EAC has been shown to facilitate the removal of stain from fabric. This finding has not been disclosed in the art.

It should be noted that other EAC derivatives can be easily prepared by the methods of the present invention. For example, EAC can further react with 1,2-dibromoethane and DL-aspartic or DL-cysteic acid to produce two possible EDC trimers; namely, diethylene aspartate dicysteate (DEADC) and diethylene diaspartate cysteate (DEDAC). The structure of the acid forms of the EAC trimers are as follows:

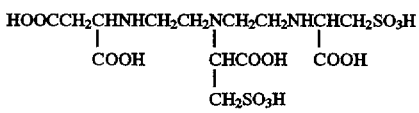

-continued

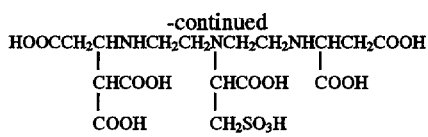

Since the EAC trimers are EAC derivatives, they can be easily substituted for EAC in the formulations of the present invention. Also, the home and industrial applications of EAC can be substituted with EAC trimers as well.

Still, it should be further noted that other EAC derivatives can be easily prepared by the methods of the present invention. For example, 1,2-dibromoethane can be replaced with epichlorohydrin, 1,3-dichloro-2-propanol or 1,3-dibromo-2-propanol. Subsequent reaction with DL-cysteic acid or L-cysteic acid monohydrate in the presence of base, water and ethanol can give a novel EAC derivative known as 2-hydroxypropylene aspartate cysteate (HPAC).

The structure of the acid form of HPAC is as follows:

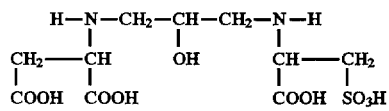

The structure of the sodium salt form of HPAC is as follows:

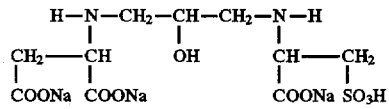

The general reaction scheme for HPAC is as follows:

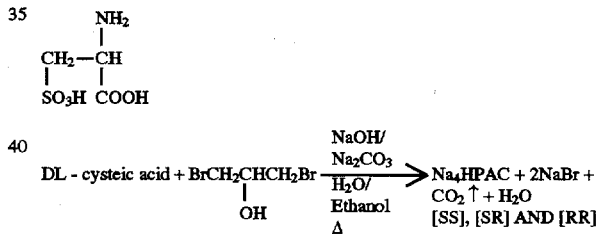

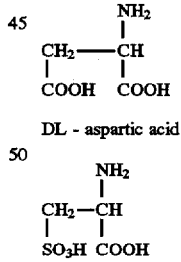

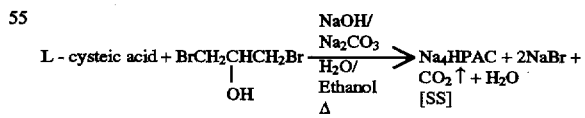

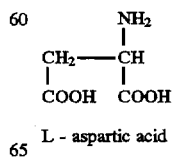

L - aspartic acid

The synthesis of HPAC from DL-cysteic acid and DL-aspartic acid yields a mixture of three optical isomers, namely; [SS], [SR] and [RR]. This is due to the presence of two asymmetric carbon atoms. Also, it is known that the biodegradation of certain amino polycarboxylates appears to be optical isomer-specific, with the [SS] isomer degrading most rapidly and extensively followed by the [SR] isomer and the [RR] isomer. Without being bound by theory, it is generally believed that the (SS) isomer of HPDC degrades most quickly and readily.

Since HPAC is an EAC derivative, it can be easily substituted for EAC in the formulations of the present invention. Also, the home and industrial applications of EAC can be substituted with HPAC as well. In fact, by simple experimentation to those skilled in the art, additional unique synergies and benefits of HPAC can be easily determined.

Finally, it should be noted that other similar sequestrants can be prepared by the methods of the present invention. For example, mixtures of DL-aspartic acid and DL-glutamic acid, can be reared with 1,2-dibromoethane, epichlorohydrin 1,3-dichloro-2-propanol, 1,3-bromo-2-propanol or mixtures thereof in the presence of base, water and ethanol to give a series of novel diaminopolycarboxylates; namely, ethylene aspartate glutamate (EAG) and 2-hydroxypropylene aspartate glutamate (HPAG).

The structure of the acid form of EAG is as follows:

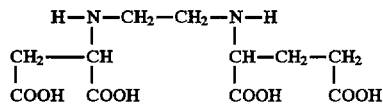

The structure of the acid form of HPAG is as follows:

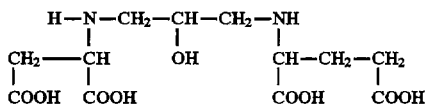

The synthesis of EAG and HPAG from DL-aspartic acid and DL-glutamic acid yields a mixture of three optical isomers; namely, [SS], [SR] and [RR]. Without being bound by theory, it is generally believed that the [SS] isomer of EAG and HPAC degrades most quickly and readily. This can be prepared by reaction with a mixture of L-aspartic acid and L-glutamic acid instead of a mixture of DLo aspartic acid and DL-glutamic acid. The sequestrants, EAG and HPAG, can be easily substituted for EAC in the formulations of the present invention. Also, the home and industrial applications of EAC can be substituted with EAG and HPAG as well. In fact, by sample experimentation to those skilled in the art, additional unique synergies and benefits of EAG and HPAG can be easily determined.

D. Optional Detersive Ingredients

Other additional optional ingredients which can be present in detergent compositions of the invention (in their conventional art-established levels for use generally from 0% to about 50% by weight of the detergent composition), include solvents, hydrotropes, solubilizing agents, processing aids, soil-suspending agents, corrosion inhibitors, dyes, fillers, optical brighteners, germicides, pH-adjusting agents, enzymes, enzyme-stabilizing agents, perfumes, fabric softening components, static control agents, dispersing agents, suds suppressing agents, thickening agents, abrasive agents, viscosity control agents, solubilizing/clarifying agents, sunscreens/UV absorbers, phase regulants, foam boosting/stabilizing agents, antioxidants, metal ions, buffering agents, color speckles, encapsulation agents, deflocculating polymers, skin protective agents, dye transfer agents, color care agents, co-sequestrants, co-chelants, bleaching agents, bleach activators, bleach stabilizers and the like.

Materials that provide clay soil removal/anti-redeposition benefits can also be incorporated in the detergent compositions of the invention and are particularly useful in liquid compositions of the invention. These clay soil removal/anti-redeposition agents are usually included at from about 0.1% to about 10% by weight of the composition.

One group of preferred clay soil removal/anti-redeposition agents are the ethoxylated amines disclosed in U.S. Pat. No. 4,597,898. Soil release agents, such as those disclosed in the art to reduce oily staining of polyester fabrics, may also be used in the compositions of the present invention. U.S. Pat. No. 3,962,152 discloses copolymers of ethylene terephthalate and polyethylene oxide terephthalate as soil release agents. Cellulose ethers and various other soil release agents are also useful.

Many additional essential and optional ingredients that are useful in the present invention are those described in McCutcheon's, *Detergents and Emulsifiers* (Vol. 1) and McCutcheon's, *Functional Materials* (Vol. 2), 1995 Annual Edition, published by McCutcheon's MC Publishing Co., as well as the CTFA (Cosmetic, Toiletry and Fragrance Association) 1992 International Buyers Guide, published by CFTA Publications and QPD 1993 Chemicals Buyers Directory 80th Annual Edition, published by Schnell Publishing Co. which are all incorporated herein by reference.

Detergent Formulations

Granular detergent compositions embodying the present invention can be formed by conventional techniques, i.e., by slurrying the individual components in water and then atomizing and spray-drying the resultant mixture, or by pan or drum agglomeration of the ingredients. Granular formulations preferably comprise from about 5% to about 60% of detergent surfactant selected from the group consisting of anionic surfactants, nonionic surfactants, and mixtures thereof.

Liquid compositions of the present invention can contain water and other solvents. Low molecular weight primary or secondary monohydric alcohols are exemplified as methanol, ethanol, propanol, and isopropanol. Monohydric alcohols are preferred for solubilizing the surfactant, but polyols, containing from about 2 to about 6 carbon atoms and from about 2 to about 6 hydroxy groups, can be used to provide improved enzyme stability (if enzymes are included in the composition). Examples of such polyols include propylene glycol, ethylene glycol, glycerine and sorbitol. Ethanol and propylene glycol are particularly preferred alcohols.

The liquid compositions preferably comprise from about 5% to about 60% of detergent surfactant, about 1% to about 30% of builder and about 0.2% to about 15% ethylene aspartate cysteate acid or salts thereof.

Useful detergency builders in liquid compositions include the alkali metal silicates, alkali metal carbonates, polyphosphonic acids, $C_8$–$C_8$ alkyl monocarboxylic acids, polycarboxylic acids, alkali metal, ammonium or substituted ammonium salts thereof, and mixtures thereof. Preferred liquid compositions contain from about 1% to about 30% of detergency builders selected from the group consisting of $C_8$–$C_8$ alkyl monocarboxylic acids, polycarboxylic acids and mixtures thereof.

Particularly, preferred liquid compositions contain from about 5% to about 18% of a $C_8$–$C_8$ monocarboxylic (fatty) acid and from about 0.2% to about 10% of a polycarboxylic acid, preferably citric acid, and provide a solution pH of from about 6 to about 10, preferably from about 6.5 to about 8.5 at a 1% concentration in water.

Preferred liquid compositions are substantially free of inorganic phosphates or phosphonates. As used in this context "substantially free" means that the liquid compositions contain less than about 0.5% by weight of an inorganic phosphate-or phosphonate-containing compound.

Many additional essential and optional ingredients that are useful in the liquid detergent compositions of the present invention are those described in McCutcheon's, *Detergents and Emulsifiers* (Vol. 1) and McCutcheon's, *Functional Materials* (Vol. 2), 1995 Annual Edition, published by McCutcheon's MC Publishing Co., as well as the CTFA (Cosmetic, Toiletry and Fragrance Association) 1992 International Buyers Guide, published by CFTA Publications and OPD 1993 Chemicals Buyers Directory 80th Annual Edition, published by Schnell Publishing Co. which are all incorporated herein by reference.

In a laundry method aspect of the invention, typical laundry wash water solutions comprise from about 0.1% to about 2% by weight of the detergent compositions of the invention. Fabrics to be laundered are agitated in these solutions to improve cleaning and stain removal characteristics of detergent compositions.

A liquid detergent composition might contain (all percentages by weight):

(1) 1–75% detergent surfactant system;
(2) 0–80% builder;
(3) 0–40% electrolyte;
(4) 0–5% enzyme;
(5) 0–15% enzyme stabilizer;
(6) 0–20% phase regulant;
(7) 0.1–50% EAC;
(8) water and additional optional ingredients to 100%.

A preferred liquid detergent composition might contain (all percentages by weight):

(1) 5–60% detergent surfactant system;
(2) 1–30% builder;
(3) 0–30% electrolyte;
(4) 0.01–4% enzyme;
(5) 00.1–14% enzyme stabilizer;
(6) 0–18% phase regulant;
(7) 0.2–15% EAC;
(8) water and additional optional ingredients to 100%

Powdered detergent composition might contain the following (all percentages by weight):

(1) 1–75% detergent surfactant system
(2) 0–80% builder;
(3) 0–30% buffer salt;
(4) 0–30% sulfate;
(5) 0–20% bleach system;
(6) 0–4% enzyme;
(7) 0.1–50% EAC;
(8) water and additional optional ingredients to 100%.

A preferred powdered detergent composition might contain the following (all percentages by weight):

(1) 5–60% detergent surfactant system
(2) 0–50% builder;
(3) 0–28% buffer salt;
(4) 0–28% sulfate;
(5) 0–18% bleach system;
(6) 0–3.5% enzyme;
(7) 0.2–15% EAC;
(8) water and additional optional ingredients to 100%.

The EAC component of the above formulations can be replaced by DEADC, DEDAC, HPAC, EAG or HPAG and mixtures thereof at the same levels of incorporation if desired.

Home Application and Use:

The EAC chelant/sequestrant and its salts of the present invention are useful in a variety of detergent, personal product, cosmetic, oral hygiene, food, pharmacological and industrial compositions which are available in many types and forms. Preferred compositions, however, are detergent compositions.

A classification according to detergent type would consist of heavy-duty detergent powders, heavy-duty detergent liquids, light-duty liquids (dishwashing liquids), institutional detergents, specialty detergent powders, specialty detergent liquids, laundry aids, pretreatments aids, after treatment aids, presoaking products, hard surface cleaners, carpet cleansers, carwash products and the like.

A classification according to personal product type would consist of hair care products, bath products, cleansing products, skin care products, shaving products and deodorant/antiperspirant products.

Examples of hair care products include, but are not limited to rinses, conditioners, shampoos, conditioning shampoos, antidandruff shampoos, antilice shampoos, coloring shampoos, curl maintenance shampoos, baby shampoos, herbal shampoos, hair loss prevention shampoos, hair growth/promoting/stimulating shampoos, hairwave neutralizing shampoos, hair setting products, hair sprays, hair styling products, permanent wave products, hair straightening/relaxing products, mousses, hair lotions, hair tonics, hair pomade products, brilliantines and the like.

Examples of bath products include, but are not limited to bath oils, foam or bubble bathes, therapeutic bathes, after bath products, after bath splash products and the like.

Examples of cleansing products include, but are not limited to shower cleansers, shower gels, body shampoos, hand/body/facial cleansers, abrasive scrub cleansing products, astringent cleansers, makeup cleansers, liquid soaps, toilet soap bars, synthetic detergent bars and the like.

Examples of skin care products include, but are not limited to hand/body/facial lotions, sunscreen products, tanning products, self-tanning products, aftersun products, masking products, lipsticks, lip gloss products, rejuvenating products, antiaging products, antiwrinkle products, anticellulite products, antiacne products and the like.

Examples of shaving products include, but are not limited to shaving creams, aftershave products, preshave products and the like.

Examples of deodorant/antiperspirant products include, but are not limited to deodorant products, antiperspirant products and the like.

A classification according to oral hygiene type would consist of, but is not Limited to mouthwashes, pre-brushing dental rinses, post-bushing rinses, dental sprays, dental creams, toothpastes, toothpaste gels, toothpowders, dental cleansers, dental flosses, chewing gums, lozenges and the like.

The EAC chelant/sequestrant of the present invention are also useful in softening compositions such as liquid fabric softeners, fabric softening rinses, fabric softening sheets, tissue papers, paper towels, facial tissues, sanitary tissues, toilet paper and the like.

A classification according to composition form would consist of aerosols, liquids, gels, creams, lotions, sprays, pastes, roll-on, stick, tablet, powdered and bar form.

Industrial Application and Use

The EAC chelant/sequestrant and its salts of the present invention are useful in a variety of compositions as above. More specifically, EAC is useful as chelants of heavy metal and hardness ions, scale inhibiting agents, corrosion inhibiting agents, deflocculating/dispensing agents, stain removal agents, bleach stabilizing agents, protecting agents of peroxygen liable ingredients, thickener/viscosity modifying agents, crystal growth modification agents, sludge modification agents, surface modification agents, processing aids, electrolyte, hydrolytic stability agents, alkalinity agents and the like. The EAC chelant/sequestrant and its salts of the present invention are also useful for certain industrial applications such as acid cleaners, aluminum etching, boiler cleaning, water treatment, bottle washing, cement modification, dairy cleaners, desalination, electrochemical machining, electroplating, metal finishing, paper mill evaporations, oil field water treatment, paper pulp bleaching, pigment dispersion, trace metal carrier for fertilizers, irrigation, circuit cleaning and the like.

The following examples further describe and demonstrate the preferred embodiments that are within the scope of the present invention. The examples are given solely for the purpose of illustration and are not to be construed as being limiting to the present invention since many variations are possible without departing from the spirit and scope of the invention.

EXAMPLE 1

Practical Synthesis of Ethylene Aspartate Cysteate (Aspartic:Cysteic Ratio=25:75)

A 500 ml three necked round bottom flask equipped with a mechanical stirrer, thermometer and reflux condenser was charged with 3.54 g (0.0266 mol) L-aspartic acid, 14.94 g (0.0798 mol) L-cysteic acid and 133 ml water. Add 8.51 g (0.2128 mol) sodium hydroxide and 5.64 g (0.0532 mol) sodium carbonate with moderate stirring. The reaction mixture exotherms to about 40° C. After all has dissolved, add 80 ml ethanol and 12.5 g (0.0665 mol) ethylene dibromide. Heat the reaction mixture to reflux (~84° C.) for 24 hours. Replace the reflux condenser with a short path distillation head and distill off the ethanol and excess ethylene dibromide. Place the flask in a water bath, heat to 70° C. and remove trace amounts of ethylene dibromide under high vacuum. The crude yield of the reaction mixture was 34.6 g. This mixture was determined to contain salt, L-aspartic acid disodium salt, L-cysteic acid disodium salt, $Na_4$ EDC, $Na_4$ EDDS and $Na_4$ EAC. The purity of this product was found to be about 50–70% sequestrant by $C^{13}$ nuclear magnetic resonance analysis.

Carbon 13 Nuclear Magnetic Resonance ($C^{13}$NMR) Analysis (Aspartic:Cysteic Ratio=25:75) (δ ppm, $D_2O$/TSP)

$$\underset{\underset{4}{COONa}}{NaO_3SCH_2\overset{2}{C}\overset{3}{H}N\overset{5}{H}CH_2} | \underset{\underset{4}{COONa}}{CH_2N\overset{5'}{H}\overset{3'}{C}H\overset{2'}{C}H_2SO_3Na} \quad Na_4EDC$$

| | Predicted (H, acid form) | Pure; Found (Na, sodium form) | Mixture; Found (Na, sodium form) |
|---|---|---|---|
| $C^2$ | 47.42 | 48.9 | 48.9 |
| $C^3$ | 53.39 | 62.8 | 62.7 |
| $C^4$ | 171.22 | 181.1 | 181.8 |
| $C^5$ | 54.14 | 55.8 | 55.9 |

$$\underset{\underset{4}{COONa}}{NaOOCCH_2\overset{2}{C}\overset{3}{H}N\overset{5}{H}CH_2} | \underset{\underset{4}{COONa}}{CH_2N\overset{5'}{H}\overset{3'}{C}H\overset{2'}{C}H_2COONa} \quad NaEDDs$$

| | Predicted (H, acid form) | Pure; Found (Na, sodium form) | Mixture; Found (Na, sodium form) |
|---|---|---|---|
| $C^{1'}$ | 177.06 | 181.5 | 181.9 |
| $C^{2'}$ | 39.89 | 41.7 | 43.8 |
| $C^{3'}$ | 54.86 | 62.8 | 62.7 |
| $C^{4'}$ | 170.14 | 180.9 | 181.8 |
| $C^{5'}$ | 53.14 | 47.4 | 48.9 |

$$\underset{\underset{4'}{COONa}}{NaOOCCH_2\overset{2'}{C}\overset{3'}{H}NHCH_2}\underset{\underset{4}{COONa}}{CH_2N\overset{3}{H}\overset{2}{C}HCH_2SO_3Na} \quad Na_4EAC$$

| | Predicted (H, acid form) | Mixture; Found (Na, sodium form) |
|---|---|---|
| $C^2$ | 47.42 | 48.9 |
| $C^3$ | 53.39 | 62.7 |
| $C^4$ | 171.22 | 181.8 |
| $C^5$ | 52.38 | 55.9 |
| $C^{1'}$ | 177.06 | 181.9 |
| $C^{2'}$ | 39.89 | 43.8 |
| $C^{3'}$ | 54.86 | 62.7 |
| $C^{4'}$ | 170.14 | 181.8 |
| $C^{5'}$ | 54.90 | 48.9 |

The above $C^{13}$ NMR analysis suggests a mixture of three sequestrants namely; $Na_4$EDC, $Na_4$ EDDS and $Na_4$ EAC.

Electrospray Mass Spectrometry (EMS) Analysis (Aspartic:Cysteic Ratio=25:75)

| | | M/Z |
|---|---|---|
| M = 452 | $Na_4$ EDC | |
| | $(M-2Na + 1H)^{-2}$ | 203 |
| | $(M-3Na + 2H)^{-2}$ | 192 |
| | $(M-4Na + 3H)^{-2}$ | 181 |
| N = 380 | $Na_4$ EDDS | |
| | $(N-4Na + 3H)^{-2}$ | 145 |
| P = 416 | $Na_4$ EAC | |
| | $(P-3Na + 2H)^{-2}$ | 174 |
| | $(P-4Na + 3H)^{-2}$ | 163 |

The above EMS analysis suggests a mixture of three sequestrants namely; $Na_4$ EDC, $Na_4$ EDDS and $Na_4$ EAC.

Capillary Electrophoresis (CE) Analysis (Aspartic:Cysteic Ratio=25:75)

| | $Na_4$ EDG | $Na_4$ EDDS | $Na_4$ EAC |
|---|---|---|---|
| Sequestrant Percent | 58.0% | 7.2% | 34.8% |
| Sequestrant Ratio | 8 | 1 | 4.8 |

The above CE analysis suggests a mixture of three sequestrants namely; $Na_4$ EDC, Na4 EDDS and $Na_4$ EAC in a ratio of 8:1:4.8 respectively.

EXAMPLE 2

Practical Synthesis of Ethylene Aspartate Cysteate (Aspartic:Cysteic Ratio=50:50)

A 500 ml three necked round bottom flask equipped with a mechanical stirrer, thermometer and reflux condenser was charged with 7.08 g (0.0532 mol) L-aspartic acid, 9.96 g (0.0532 mol) L-cysteic acid and 133 ml water. Add 8.51 g (0.2128 mol) sodium hydroxide and 5.64 g (0.0532 mol) sodium carbonate with moderate stirring. The reaction mixture exotherms to about 40° C. After all has dissolved, add 80 ml ethanol and 12.5 g (0.0665 mol) ethylene dibromide. Heat the reaction mixture to reflux (84° C.) for 24 hours. Replace the reflux condenser with a short path distillation head and distill off the ethanol and excess ethylene dibromide. Place flask in a water bath heated at 70° C. and remove trace amounts of ethylene dibromide under high vacuum. The crude yield of the reaction mixture was 31.08 g. This mixture was determined to contain salt, L-aspartic acid disodium salt, L-cysteic acid disodium salt, $Na_4$ EDC, $Na_4$ EDDS and $Na_4$ EAC. The purity of this product was found to be about 50–70% sequestrant by C is nuclear magnetic resonance analysis.

Electrospray Mass Spectrometry (EMS) Analysis
(Aspartic:Cysteic ratio=50:50)

|  |  | M/Z |
|---|---|---|
| M = 452 | $Na_4$ EDC | |
| | $(M-3Na + 2H)^{-2}$ | 192 |
| | $(M-4Na + 3H)^{-2}$ | 181 |
| N = 380 | $Na_4$ EDDS | |
| | $(N-4Na + 3H)^{-2}$ | 145 |
| P = 416 | $Na_4$ EAC | |
| | $(P-4Na + 3H)^{-2}$ | 163 |

The above EMS analysis suggests a mixture of three sequestrants namely; $Na_4$ EDC, $Na_4$ EDDS and $Na_4$ EAC.

Capillary Electrophoresis (CE) Analysis
(Aspartic:Cysteic Ratio=50:50)

|  | $Na_4$ EDC | $Na_4$ EDDS | $Na_4$ EAC | UNKNOWN |
|---|---|---|---|---|
| Sequestrant Percent | 19.2% | 29.1% | 47.9% | 3.8% |
| Sequestrant Ratio | 1 | 1.5 | 2.5 | — |

The above analysis suggests a mixture of three sequestrants namely; $Na_4$ EDC, $Na_4$ EDDS and $Na_4$ EAC in a ratio of 1:1.5:2.5 respectively.

EXAMPLE 3

Practical Synthesis of Ethylene Aspartate Cysteate
(Aspartic:Cysteic Ratio=75:25)

A 500 ml three necked round bottom flask equipped with a mechanical stirrer, thermometer and reflux condenser was charged with 10.62 g (0.0798 mol) L-aspartic acid, 4.98 g (0.0266 mol) L-cysteic acid and 133 ml water. Add 8.51 g (0.2128 mol) sodium hydroxide and 5.64 g (0:0532 mol) sodium carbonate with moderate stirring. The reaction mixture exotherms to about 40° C. After all has dissolved, add 80 ml ethanol and 12.5 g (0.0665 mol) ethylene dibromide. Heat the reaction mixture to reflux (84° C.) for 24 hours. Replace the reflux condenser with a short path distillation head and distill off the ethanol and excess ethylene dibromide. Place flask in a water bath heated at 70° C. and remove trace amounts of ethylene dibromide under high vacuum. The crude yield of the reaction mixture was 31.35 g. This mixture was determined to contain salt, L-aspartic acid disodium salt, L-cysteic acid disodium salt, $Na_4$ EDC, $Na_4$ EDDS and $Na_4$ EAC. The purity of this product was found to be about 50–70% sequestrant by $C^{13}$ nuclear magnetic resonance analysis.

Electrospray Mass Spectrometry (EMS) Analysis
(Aspartic:Cysteic Ratio 75:25)

|  |  | M/Z |
|---|---|---|
| M = 452 | $Na_4$ EDC | |
| | $(M-2a + 1H)^{-2}$ | 203 |
| | $(M-3a + 2H)^{-2}$ | 192 |
| | $(M-4a + 3H)^{-2}$ | 181 |
| N = 380 | $Na_4$ EDDS | |
| | $(N-2a + 1H)^{-2}$ | 167 |
| | $(N-3a + 2H)^{-2}$ | 156 |
| | $(N-4Na + 3H)^{-2}$ | 145 |
| P = 416 | $Na_4$ EAC | |
| | $(P-2Na + 1H)^{-2}$ | 185 |
| | $(P-3Na + 2H)^{-2}$ | 174 |
| | $(P-4Na + 3H)^{-2}$ | 163 |

The above EMS analysis suggests a mixture of three sequestrants namely; $Na_4$ EDC, $Na_4$ EDDS and $Na_4$ EAC.

Capillary Electrophoresis (CE) Analysis
(Aspartic:Cysteic Ratio=75:25)

|  | $Na_4$ EDC | $Na_4$ EDDS | $Na_4$ EAC | Unknown |
|---|---|---|---|---|
| Sequestrant Percent | 2.8% | 62.4% | 29.0% | 5.8% |
| Sequestrant Ratio | 1 | 22.3 | 10.4 | — |

The above CE analysis suggests a mixture of three sequestrants namely; $Na_4$ EDC, $Na_4$ EDDS and $Na_4$ EAC in a ratio of 1:22.3:10.4 respectively.

EXAMPLE 4

Purification of Ethylene Aspartate Cysteate

A 5 g sample of Example 2 is purified by trituration with methanol and water, followed by dissolution in 10 ml water. Adjust the pH of the solution to 4–5 with hydrochloric acid to precipitate EAC. Use column chromatography to purify EAC.

EXAMPLE 5

Purification of Ethylene Aspartate Cysteate

A 5 g sample of Example 2 is dissolved in 25 ml of water. Adjust the pH of the solution to 3 with hydrochloric acid. To this solution add calcium hydroxide until the pH is 11. Stir for about an hour at 25° C. during which time a white solid precipitates. Filter the white precipitate and wash with cold water. Using ion exchange chromatography, substitute the calcium ions for sodium ions and adjust the pH of EAC elulent with sodium carbonate to 8.0–9.0.

EXAMPLE 6

Purification of Ethylene Aspartate Cysteate

A 5 g sample of Example 1 is purified by high pressure liquid chromatography to give pure samples of EDC, EAC and EDDS.

EXAMPLE 7

Synthesis of Ethylene Asparate Glutamate
(Aspartic:Glutamic Ratio 50:50)

A 500 ml three necked round bottom flask equipped with a mechanical stirrer, thermometer and reflux condenser is charged with 7.08 g (0.0532 mol) L-aspartic acid 7.83 g (0.0532 mol) L-glutamic acid and 133 ml water. Add 8.51 g (0.2128 mol) sodium hydroxide and 5.64 g (0.0332 mol) sodium carbonate with moderate stirring. The reaction mixture exotherms to about 40° C. After all has dissolved, add 80 ml ethanol and 12.5 g (0.0665 mol) ethylene dibromide. Heat the reaction mixture to reflux (84° C.) for 24 hours. Replace the reflux condenser with a short path distillation head and distill off the ethanol and excess ethylene dibromide to about half volume. Place the reaction mixture on a rotoevaporater and distill to about 55 ml volume. Acidity the solution to pH of 3 with concentrated hydrochloric acid. Cool in a refrigerator overnight. Filter the white solid and wash with cold water. Analysis of the product by NMR suggests the presence of aspartic acid and glutamic acid. Place white solid in a round bottom flask and add 55 ml of water. Adjust the pH of the solution of about 8–9.5 and stir for 15 minutes. Acidity the solution to a pH of about 4. Filter the resulting white crystalline solid and wash with water. Dry in an oven at 35° C. under high vacuum for 24 hours. Analysis of the product suggests a mixture of ethylene asparticglutamic acid, ethylenediamine disuccinic acid and ethylenediamine diglutamic acid.

EXAMPLE 8

Preparation of 2-Hydroxypropylene Aspartate Cysteate (Aspartate:Cysteate Ratio 50:50)

8.5 g (0.064 mol) of L-aspartic acid and 12 g (0.0641 mol) L-cysteic acid is dissolved in 160 ml of water containing 10.2 g (0.255 mol) of sodium hydroxide. After dissolution, 6.8 g (0.064) sodium carbonate is added, followed by 80 ml ethanol. While refluxing the solution, 16.8 g (0.077 mol) 1,3-dibromo-2-propanol is added gradually during a period of 4 hours, followed by refluxing overnight. An additional 16.8 g (0.077 mol) of 1,3-dibromo-2-propanol is added, followed by all-day reflux. The solution is distilled to remove solvents and the resulting solid which contains HPAC and other materials is recovered and triturated with methanol/water. The purified solid is triturated again with methanol only and stirred overnight to remove residual materials, followed by dissolution in 10 cc water. Adjustment of the solution pH to 3–5 precipitates out HPAC. The final product is further purified by high pressure liquid chromotography.

EXAMPLES 9–14

To further demonstrate the stain removal characteristics of detergent compositions containing EAC, a commercial detergent composition was obtained containing EAC and compared to an identical composition containing either NTA, EDTA, EDC or DETPA. The latter chelates, EDTA and DETPA are not readily biodegradable. The structure of the chelants are as follows:

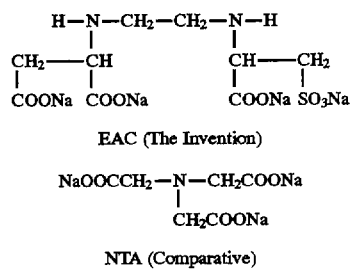

EAC (The Invention)

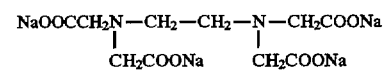

NTA (Comparative)

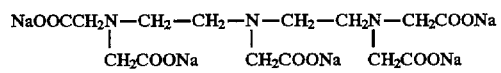

EDTA (Comparative)

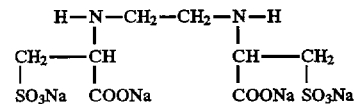

DETPA (Comparative)

H—N—CH₂—CH₂—N—H
|                    |
CH₂——CH      CH——CH₂
|     |            |     |
SO₃Na COONa  COONa SO₃Na

EDC (Comparative)

A great number of test methods have been developed to determine the performance of detergents and various detergent ingredients. A preferred, well-accepted test method involves applying various soils uniformly to a standard cloth under strict specifications yielding an "artificially soiled test cloth", which is then washed under controlled conditions in a Terg-o-tometer (washing machine simulator). The detergency of the sequestrant is assessed electronically using a reflectometer (Colorgard 2000). Before washing, the initial reflectance value of the soiled test cloth is measured (front and back) giving a value which is represented as reflectance-soiled ($R_s$). After washing, the final reflectance value of the soiled test cloth is measured (front and back) giving a value which is represented as reflectance-washed ($R_w$). From these values, the differences in reflectance $\Delta R = R_w - R_s$ can be calculated and used as a measure of soil removal. It shall be understood that higher $\Delta R$ values suggests better or enhanced detergency.

In general, textiles come in contact with a variety of soils, some of which are complicated mixtures of materials differing in their chemical and physical structure. The selection of a model soil representing a natural "real life" soil is a complicated problem. However, significant progress has been made in the area of fabric washing making artificial soiling more realistic. Since it is not practical to test the surfactant detergency with every possible soil that may be encountered, it must therefore be limited to typical model soils representing the most common natural soils. Artificial soils are usually selected to represent the following four types of common natural soils which includes (1) particulate soils, (2) fatty soils, (3) stains and (4) oily soils.

The stain removal characteristics of EAC was determined on EMPA 114 cloth, CS-15, test fabrics coffee cloth, test fabrics tea cloth and WFK 20D cloth. Each of the cloths were soiled with the following materials:

| CLOTH | SOIL |
|---|---|
| EMPA 114 | Cotton cloth soiled with red wine (stain) |
| CS-15 | Cotton cloth soiled with blueberry (stain) |
| Test fabrics coffee | Cofton cloth soiled with coffee (stain) |
| Test fabrics tea | Cotton cloth soiled with tea (stain) |
| WFK 20D | Polyester/cotton cloth (65:35) soiled with pigment and sebum (particulate, fatty and oily soil) |

The WFK synthetic pigment consists of:

| | |
|---|---|
| 86.0% | Kaolinite |
| 8.0% | Flame Soot 101 |
| 4.0% | Iron Oxide Black |
| 2.0% | Iron Oxide Yellow |
| 100% | |

The WFK synthetic sebum consists of:

| | |
|---|---|
| 18.0% | Free Fatty Acids |
| 32.8% | Beef Tallow |
| 3.6% | Fatty Acid Triglycerides |
| 18.3% | Lanoline |
| 3.7% | Cholesterol |
| 12.0% | Hydrocarbon Mixture |
| 11.6% | Cutina |
| 100% | |

The wash conditions used to evaluate EAC are as follows:

| WASH CONDITIONS FOR EAC | |
|---|---|
| Apparatus | Terg-o-tometer |
| Wash Time | 20 mins. |
| Agitation | 70 rpm |
| Wash Liquid Volume | 1000 ml |
| Base Liquid | Wisk |
| Dosage | 6.0 g/l |
| pH | 8.5 |
| Hardness | 24 FH (4:1 Ca:Mg) |
| Metal ions | 2.3 ppm $Zn^{+2}$, 2 ppm $Fe^{+3}$, 1.1 ppm $Cu^{+2}$, 0.12 ppm $Mn^{+2}$ |
| Temperature | 40° C. |
| Test cloths | Four 3 × 4 cloths per pot (single stain) |
| Washes | 1 to 3 separate washes |

Procedure:

1) Add DI water, hardness and metal ions
2) Add Wisk liquid detergent
3) Add Sequestrant
4) Add Cloth
5) Wash (20 min)
6) Rinse (1 min)
7) Dry in the Dryer (10 min.)

Sequestrant:
a) EAC (The Invention)
b) NTA (Comparative)
c) EDTA (Comparative)
d) DETPA (Comparative)

Sequestrant Concentration: 1–20% by weight of commercial Wisk detergent formulation.

A commercially available heavy duty liquid detergent (Wisk) was used with various levels of EAC (1–20%). This was compared to an identical composition containing either NTA, EDTA or DETPA. The test was performed in a terg-o-tometer. Water containing the appropriate hardness and heavy metal ions were added followed by the addition of Wisk liquid detergent. The chelant was then added to the wash water in an amount sufficient to make the levels of the chelant either 1% or 20% by weight of the liquid detergent. Finally, artificially soiled 3×4 fabrics were added and washed for 20 mins. The fabrics were than rinsed and dried in a dryer. One or three replicates of each treatment was conducted. The mean scores for each treatment were calculated and are represented as ΔR. It shall be understood that higher ΔR values suggest better or enhanced detergency/cleaning. A statistical value was assigned to each score at a 95% confidence limit to counterbalance any variation associated with the test and to provide a reliable range associated with the mean. The results are shown below in Examples 9–14.

EXAMPLE 9

Stain Removal Characteristics of (50:50) EAC in Wisk Liquid Detergent

| COFFEE (TEST FABRICS) | | | | |
|---|---|---|---|---|
| | | | 95% Confidence Limit | |
| Chelant | One Wash Mean ΔR | | Low | High |
| 0% (No Chelant) | 25.9 ± 0.6 | = | 25.3 | 26.5 |
| 1% EAC | 28.4 ± 0.2 | = | 28.2 | 28.6 |
| 3% EAC | 29.6 ± 0.3 | = | 29.3 | 29.9 |
| 5% EAC | 31.6 ± 0.3 | = | 31.3 | 31.9 |
| 7% EAC | 31.6 ± 0.2 | = | 31.8 | 31.4 |
| 20% EAC | 33.7 ± 0.4 | = | 33.3 | 34.1 |
| 3% EDC (Comparative) | 29.2 ± 0.6 | = | 28.6 | 29.8 |

EAC is derived from a mixture of aspartic acid and cysteic acid (50:50).

From the above table, it can be seen that EAC, with a higher mean ΔR value, provides improved cleaning on polyphenolic coffee stain over the Wisk formulation without a chelant (0%). This improvement was found to be statistically equivalent to EDC.

EXAMPLE 10

Stain Removal Characteristics of (50:50) EAC in Wisk Liquid Detergent

| TEA (TEST FABRICS) | | | | |
|---|---|---|---|---|
| | | | 95% Confidence Limit | |
| Chelant | One Wash Mean ΔR | | Low | High |
| 0% (No Chelant) | 15.4 ± 0.5 | = | 14.4 | 15.9 |
| 1% EAC | 20.8 ± 1.6 | = | 19.2 | 22.4 |
| 3% EAC | 21.7 ± 0.9 | = | 20.8 | 22.6 |
| 5% EAC | 22.1 ± 0.6 | = | 21.5 | 22.7 |
| 7% EAC | 23.3 ± 0.5 | = | 22.8 | 23.3 |
| 3% EDC (Comparative) | 21.1 ± 0.7 | = | 20.4 | 21.8 |

EAC is derived from a mixture of aspartic acid and cysteic acid (50:50).

From the above table, it can be seen that EAC, with a higher mean ΔR value, provides improved cleaning on polyphenolic tea stain over the Wisk formulation without a chelant (0%). This improvement was found to be statistically equivalent to EDC.

EXAMPLE 11

Stain Removal Characteristics of (25:75) EAC in Wisk Liquid Detergent

| | CS-15-005 BLUEBERRY | | |
|---|---|---|---|
| | | 95% Confidence Limit | |
| Chelant | One Wash Mean ΔR | Low | High |
| 0% (No Chelant) | 30.7 ± 0.7 = | 30.0 | 31.4 |
| 1% EAC | 33.2 ± 0.6 = | 32.6 | 33.2 |
| 3% EAC | 34.4 ± 0.7 = | 33.7 | 35.1 |
| 5% EAC | 34.1 ± 0.8 = | 33.3 | 34.9 |
| 7% EAC | 34.6 ± 0.7 = | 33.9 | 35.3 |
| 20% EAC | 35.2 ± 0.7 = | 34.5 | 35.9 |
| 3% EDC (Comparative) | 33.5 ± 0.8 = | 32.7 | 34.3 |

EAC is derived from a mixture of aspartic acid and cysteic acid (25:75).

From the above table, it can be seen that EAC, with a higher mean ΔR value, provides improved cleaning on polyphenolic blueberry stain over the Wisk formulation without a chelant (0%). This improvement was found to be statistically equivalent to EDC.

EXAMPLE 12

Stain Removal Characteristics of (50:50) EAC in Wisk Liquid Detergent

| | CS-15-005 BLUEBERRY | | |
|---|---|---|---|
| | | 95% Confidence Limit | |
| Chelant | One Wash Mean ΔR | Low | High |
| 0% (No Chelant) | 30.7 ± 0.7 = | 30.0 | 31.4 |
| 1% EAC | 33.7 ± 0.7 = | 33.0 | 34.4 |
| 3% EAC | 34.4 ± 0.7 = | 33.7 | 35.1 |
| 5% EAC | 34.5 ± 0.6 = | 33.7 | 35.1 |
| 7% EAC | 35.4 ± 0.6 = | 33.9 | 35.1 |
| 3% EDC (Comparative) | 33.5 ± 0.8 = | 32.7 | 34.3 |

EAC is derived from a mixture of aspartic acid and cysteic acid (50:50).

From the above table, it can be seen that EAC, with a higher mean ΔR value, provides improved cleaning on polyphenolic blueberry stain over the Wisk formulation without a chelant. This improvement was found to be statistically equivalent to EDC.

EXAMPLE 13

Stain Removal Characteristics of (75:25) EAC in Wisk Liquid Detergent

| | CS-15-005b BLUEBERRY | | |
|---|---|---|---|
| | | 95% Confidence Limit | |
| Chelant | One Wash Mean ΔR | Low | High |
| 0% (No Chelant) | 22.5 ± 0.2 = | 22.3 | 22.7 |
| 1% EAC | 25.7 ± 0.3 = | 25.4 | 26.0 |

-continued

| | CS-15-005b BLUEBERRY | | |
|---|---|---|---|
| | | 95% Confidence Limit | |
| Chelant | One Wash Mean ΔR | Low | High |
| 3% EAC | 26.0 ± 0.2 = | 25.8 | 26.2 |
| 5% EAC | 25.9 ± 0.3 = | 25.6 | 26.2 |
| 7% EAC | 26.0 ± 0.2 = | 25.8 | 26.2 |
| 20% EAC | 25.8 ± 0.3 = | 25.6 | 26.0 |

EAC is derived from a mixture of aspartic acid and cysteic acid (75:25).

From the above table, it can be seen that EDC, with a higher mean ΔR value, provides improved cleaning on polyphenolic blueberry stain over the Wisk formulation without a chelant.

EXAMPLE 14

Stain Removal Characteristics of Chelants

| | EMPA 114 (Wine) | | |
|---|---|---|---|
| | | 95% Confidence Limit | |
| Chelant | One Wash Mean ΔR | Low | High |
| 0% (No Chelant) | 23.1 ± 0.4 = | 22.7 | 23.5 |
| 3% EAC (The Invention) | 28.0 ± 0.6 = | 27.5 | 28.5 |
| 3% NTA (Comparative) | 26.8 ± 0.4 = | 26.4 | 27.2 |
| 3% EDTA (Comparative) | 26.7 ± 0.4 = | 26.3 | 27.1 |
| 3% DETPA (Comparative) | 27.7 ± 0.4 = | 27.3 | 28.1 |

EAC is derived from a mixture of aspartic acid and cysteic acid (50:50).

From the above table, it can be seen that EAC, with a higher mean ΔR value, provides improved cleaning on polyphenolic wine stain over the base formulation without a chelant. This improvement was found to be statistically equivalent to DETPA, but statistically bearer than NTA and EDTA. This finding is new and has not been disclosed in the art.

EXAMPLE 15

Stain Removal Characteristics of (25:75)

| | WFK20 (Pigment/Sebum) | | |
|---|---|---|---|
| | | 95% Confidence Unit | |
| Chelant | One Wash Mean ΔR | Low | High |
| 0% (No Chelant) | 10.4 ± 0.5 = | 9.9 | 10.9 |
| 3% EAC | 11.3 ± 0.6 – | 10.7 | 11.9 |
| 3% EDC (Comparative) | 11.1 ± 0.4 = | 10.7 | 11.5 |

EAC is derived from a mixture of aspartic acid and cysteic acid (25:75).

From the above table, it can be seen that EAC, with a higher mean ΔR value, provides improved cleaning on oily fatty type soil. However, this improvement was found to be statistically the same as the WISK formulation without a chelant (0%) and EDC.

EXAMPLES 16–19

The following Examples (16–19) represent the frame formulations of the present invention. These Examples are not intended to be limiting to be present invention, but rather to simply further illustrate the additional aspects of the present technology which may be considered by the formulator when manufacturing a wide variety of detergent compositions comprising EAC chelant/sequestrant. Numerous modifications and variations are possible without departing from the spirit and scope of the present frame formulations. Unless otherwise indicated, all percentages herein are by weight.

EXAMPLE 16

General Frame Formulations for Heavy-Duty Detergent Powders

| INGREDIENTS (BY WEIGHT) | USA CANADA AUSTRALIA | SO. AMERICA MIDDLE EAST AFRICA | EUROPE | JAPAN |
|---|---|---|---|---|
| Cleansing agents | 8–30 | 10–32 | 8–28 | 5–29 |
| EAC Chelant/Sequestrant | 0.1–50 | 0.1–50 | 0.1–50 | 0.1–50 |
| Bleach | 0–27 | 0–7 | 0–30 | 0–7 |
| Anti-corrosion agents | 0–25 | 03.–12 | 1–9 | 4–15 |
| Builders | 5–45 | 5–45 | 2–35 | 0–25 |
| Cobuilders (alkalis) | 0–35 | 0–40 | 0–15 | 5–20 |
| Optical brighteners | 0–0.5 | 0–0.5 | 0–0.4 | 0–0.9 |
| Anti-redeposition agents | 0–3 | 0.2–2 | 0.3–4 | 0–2 |
| Enzymes | 0–2.7 | 0–0.8 | 0–1 | 0–0.8 |
| Foam-boosting agents | 0–2 | 0–2 | 0–2 | — |
| Suds-suppression agents | 0.01–3.5 | 0.01–3 | 0.01–4 | 0.01–3 |
| Fillers | 5–45 | 5–39 | 5–45 | 3–45 |
| Water | 6–20 | 6–13 | 4–20 | 5–10 |
| Additional detersive ingredients | Balance | Balance | Balance | Balance |

EXAMPLE 17

Additional Frame Formulations for Heavy-Duty Detergent Powders

| INGREDIENTS (BY WEIGHT) | USA | EUROPE | JAPAN |
|---|---|---|---|
| Anionic Surfactants | | | |
| Alkylbenzene sulfonates | 5–20 | 5–22 | 5–27 |
| Alkyl sulfates | 0–20 | 0–25 | 0–15 |
| Alkyl ether sulfates | 0–20 | — | — |
| α-Olefin sulfonates | 0–5 | 0–15 | 0–15 |
| Nonionic Surfactants | | | |
| Alcohol ethoxylates | 3–17 | 3–12 | 0–10 |
| Nonylphenol ethoxylates | 0–5 | 0–5 | — |
| Alkyl polyglycosides | 0–15 | 0–15 | 0–15 |
| Alkyl methyl glycamides | 0–18 | 0–18 | 0–18 |
| Alkyl Aldonamides/Aldobionamides | 0–25 | 0–25 | 0–25 |
| EAC Chelant/Sequestrant | 0.1–50 | 0.1–50 | 0.1–50 |
| Bleaching Agents | | | |
| Sodium perborate | 0–27 | 0–30 | 0–7 |
| Sodium percarbonate | 0–27 | 0–30 | 0–7 |
| Bleach Activators | | | |
| Tetraacetyl ethylenediamine (TAED) | 0–5 | 0–8 | 0–8 |
| Sodium nonanoyloxybenzene sulfonate | 0–10 | 0—10 | 0–7 |
| Manganese IV complex agent | 0–0.5 | 0–0.5 | 0–0.5 |
| Anti-Corrosion Agents | | | |
| Sodium silicate | 0–25 | 1–9 | 4–15 |
| Builders (Ion Exchange) | | | |
| Zeolites | 5–49 | 2–35 | 0–25 |
| Polyacrylates | 0–9 | 0–8 | 0–7 |
| Builders | | | |
| Sodium citrate | 0–18 | 0–5 | 5–23 |
| Sodium tartrate mono-/disuccinate | 0–15 | 0–5 | — |
| Co-builders (Alkalis) | | | |
| Sodium carbonate | 0–35 | 0–15 | 5–20 |
| Co-chelating Agents | | | |
| Ethylene diaminetetraacetates (EDTA) | 0–1 | 0–0.5 | — |
| Optical Brighteners | | | |
| Stilbene-disulfonic acid - derivatives | 0–0.5 | 0–0.4 | 0–0.9 |
| Bis-(styryl)-biphenyl derivatives | 0–0.5 | 0–0.4 | 0–0.9 |
| Anti-Redeposition Agents | | | |
| Sodium carboxymethyl cellulose | 0–1.5 | 0.3–2 | 0–2.8 |
| Cellulose ethers | 0–1.5 | 0.3–2 | 0–2 |
| Polyethylene glycols | 0–3 | 0–4 | 0–2 |
| Enzymes | | | |
| Proteases | 0–2.7 | 0–1 | 0–0.8 |
| Amylases | 0–1 | 0–1 | 0–0.8 |
| Foaming Boosting Agents | | | |
| Alkanolamides | 0–2 | 0–2 | — |
| Suds-Suppression Agents | | | |
| Silicon oils | 0.01–1 | 0.01–4 | 0.01–3 |
| Fatty acid soaps | 0–3.5 | 0–4 | 0–3 |
| Fabric Softening Agents | | | |
| Quats | 0–5 | — | 0–6 |
| Clays | 0–5 | — | 0–6 |
| Fillers | | | |
| Sodium sulfate | 5–45 | 3–45 | 30–45 |
| Fragrances | 0–1 | 0–1 | 0–1 |
| Dyes/Blueing Agents | 0–1 | 0–1 | 0–1 |
| Water | 6–20 | 4–20 | 5–10 |
| Formulation Aids | 0–1 | 0–1 | 0–1 |
| Additional Detersive Ingredients | Balance | Balance | Balance |

EXAMPLE 18

Frame Formulations for Heavy-Duty Detergent Liquids (Built and Unbuilt)

|  | USA | | EUROPE | | JAPAN | |
| --- | --- | --- | --- | --- | --- | --- |
| INGREDIENTS (BY WEIGHT) | BUILT | UNBUILT | BUILT | UNBUILT | BUILT | UNBUILT |
| Anionic Surfactants | | | | | | |
| Alkylbenzene sulfonates | 5–27 | 0–20 | 5–17 | 10–25 | 5–25 | 0–23 |
| Alkyl sulfates | 0–15 | 0–15 | 0–22 | 0–25 | 0–23 | 0–18 |
| Alkyl ether sulfates | 0–25 | 0–22 | 0–20 | 0–22 | 5–20 | 15–25 |
| α-Olefin sulfonates | 0–14 | — | — | 0–15 | 0–20 | — |
| Nonionic Surfactants | | | | | | |
| Alcohol ethoxylates | 5–11 | 15–35 | 2–10 | 10–15 | 4–10 | 10–35 |
| Nonylphenol ethoxylates | 0–15 | 0–15 | 0–12 | 0–14 | 0–14 | 0–14 |
| Alkyl polyglycosides | 0–15 | 0–15 | 0–12 | 0–14 | 0–15 | 0–15 |
| Alkyl methyl glycamides | 0.1–45 | 0.1–45 | 0–45 | 0.1–45 | 0.1–45 | 0.1–45 |
| Alkyl Aldanamides/Aldobionamides | 0–45 | 0–45 | 01–45 | 9–45 | 0–45 | 0–45 |
| EAC Chelant/Sequestrant | 0.1–50 | 0.1–50 | 0.1–50 | 0.1–50 | 0.1–50 | 0.1–50 |
| Anti-Corrosion Agents | | | | | | |
| Sodium silicate | 0–12 | — | — | 0–3 | 3–7 | — |
| Builders | | | | | | |
| Sodium citrate | 1–12 | — | 1–5 | — | 3–7 | — |
| Co-chelating Agents | | | | | | |
| Ethylene diaminetetraacetates (EDTA) | — | — | — | 0–3 | 0–3 | 0–5 |
| Optical Brighteners | | | | | | |
| Stilbene-disulfonic acid-derivatives | 0–0.3 | 0–0.3 | 0–0.3 | 0–0.3 | 0–0.4 | 0–0.4 |
| Bis-(styryl)-biphenyl derivatives | 0–0.4 | 0–0.4 | 0–0.4 | 0–0.4 | 0–0.4 | 0–0.4 |
| Enzymes | | | | | | |
| Proteases | 0–1.8 | 0–2.5 | 0–0.5 | 0–1 | 0–0.5 | 0–1 |
| Enzyme Stabilizing Agents | | | | | | |
| Triethanolamine | 0–3 | 0–4 | 0–3 | 0–4 | 0–5 | 0–5 |
| Foaming Boosting Agents | | | | | | |
| Alkanolamides | — | — | 0–2 | — | — | — |
| Suds-Suppression Agents | | | | | | |
| Fatty acid soaps | — | — | 0–2 | — | — | — |
| Fabric Softening Agents | | | | | | |
| Quats | 0–2 | — | — | — | — | — |
| Clays | 0–2 | — | — | — | — | — |
| Hydrotropes/Salubilizing Agents | | | | | | |
| Xylene sulfonates | 0–14 | 0–12 | 0–6 | 0–12 | 0–15 | 0–15 |
| Ethanol | 7–14 | 5–12 | 3–6 | 6–12 | 10–15 | 5–15 |
| Propylene glycol | 7–14 | 5–12 | 3–10 | 6–14 | 5–15 | 5–18 |
| Fragrances | 0–1 | 0–1 | 0–1 | 0–1 | 0–1 | 0–1 |
| Dyes/Blueing Agents | 0–1 | 0–1 | 0–1 | 0–1 | 0–1 | 0–1 |
| Water and Additional Detersive Ingredients | Balance | Balance | Balance | Balance | Balance | Balance |

EXAMPLE 19

Frame Formulations for Light-Duty Dishwashing Detergent Liquids

| INGREDIENTS (BY WEIGHT) | DISHWASHING LIQUID |
| --- | --- |
| Anionic Surfactants | |
| Alkylbenzene sulfonates | 1–25 |
| Alkyl sulfates | 2–10 |
| Alkyl ether sulfates | 2–23 |
| Fatty acid soaps | 0–3 |
| Nonionic Surfactants | |
| Alcohol ethoxylates | 0–15 |
| Alkyl polyglycosides | 0–20 |
| Alkyl methyl glycamides | 0–18 |
| Alkyl Aldonamides/Aldobionamides | 0–30 |
| Amphoteric Surfactants | |
| Alkyl betaines | 0–3 |
| EAC Chelant/Sequestrant | 0.1–50 |
| Builders | |
| Sodium citrate | 0–5 |
| Co-chelating Agents | |
| Ethylene diaminetetraacetates (EDTA) | 0–3 |
| Foaming Boosting Agents | |
| Alkanolamides | 0–8 |
| Hydrotropes/Solubilizing Agents | |
| Xylene sulfonates | 0–2 |
| Ethanol | 0–10 |
| Viscosity Modifying Agent | |
| Sodium chloride | 0–4 |
| Ions | |
| Magnesium sulfate | 0–2 |
| Opacifiers | 0–2 |
| Fragrances | 0–1 |
| Dyes | 0–1 |
| Water and Additional Detersive Ingredients | Balance |

EXAMPLE 20

The EAC component of Examples 2–5 is replaced by EAC trimer at the same levels of incorporation.

EXAMPLE 21

The EAC component of Examples 16–19 is replaced by a mixture of EAC trimer and EAC at the same levels of incorporation.

EXAMPLE 22

The EDC component of Examples 16–19 is replaced by HPDC at the same levels of incorporation.

EXAMPLE 23

The EDC component of Examples 16–19 is replaced by a mixture of HPAC and EAC at the same levels of incorporation.

EXAMPLE 24

The EDC component of Examples 16–19 is replaced by a mixture of HPAC, EAC trimer and EAC at the same levels of incorporation.

EXAMPLE 25

Preparation of 2-Hydroxypropylene Aspartate Glutamate (Aspartic:Glutamic Ratio 50:50)

8.5 g (0.064 mol) of L-aspartic acid and 9.4 g (0.0641 mol) L-glutamic acid is dissolved in 160 ml of water containing 10.2 g (0.255 mol) of sodium hydroxide. After dissolution, 6.8 g (0.064) sodium carbonate is added, followed by 80 ml ethanol. While refluxing the solution, 16.8 g (0.077 mol) 1,3-dibromo-2-propanol is added gradually during a period of 4 hours, followed by refluxing overnight. An additional 16.8 g (0.077 mol) of 1,3-dibromo-2-propanol is added, followed by all-day reflux. The solution is distilled to remove solvents and the resulting solid which contains HPAC and other materials is recovered and triturated with methanol/water. The purified solid is triturated again with methanol only and stirred overnight to remove residual materials, followed by dissolution in 10 cc water. Adjustment of the solution pH to 3–5 precipitates out HPAG. The final product is further purified by high pressure liquid chromotography.

EXAMPLE 26

The EDC component of Examples 16–19 is replaced by a mixture of HPAG at the same levels of incorporation.

EXAMPLE 27

The EDC component of Examples 16–19 is replaced by EAG at the same levels of incorporation.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A compound of the formula:

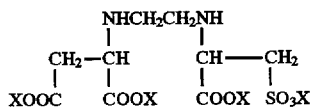

wherein X is independently selected from the group consisting of hydrogen, sodium, potassium, lithium, ammonium, monoethanolammonium, diethanolammonium, triethanolammonium and mixtures thereof.

2. A compound as defined in claim 1 wherein X is hydrogen.

3. A compound as defined in claim 1 wherein X is sodium.

4. A compound as defined in claim 1 wherein X is monoethanolamine.

5. A compound as defined in claim 1 wherein X is triethanolamine.

6. A compound of the formula:

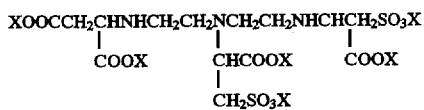

wherein X is independently selected from the group consisting of hydrogen, sodium, potassium, lithium, ammonium, monoethanolammonium, diethanolammonium, triethanolammonium and mixtures thereof.

7. A compound as defined in claim 6 wherein X is hydrogen.

8. A compound as defined in claim 6 wherein X is sodium.

9. A compound as defined in claim 6 wherein X is monoethanolamine.

10. A compound as defined in claim 6 wherein X is triethanolamine.

11. A compound of the formula:

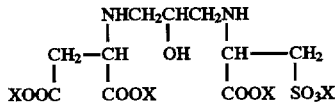

wherein X is independently selected from the group consisting of hydrogen, sodium, potassium, lithium, ammonium, monoethanolammonium, diethanolammonium, triethanolammonium and mixtures thereof.

12. A compound as defined in claim 11 wherein X is hydrogen.

13. A compound as defined in claim 11 wherein X is sodium.

14. A compound as defined in claim 11 wherein X is monoethanolamine.

15. A compound as defined in claim 11 wherein X is triethanolamine.

16. A compound of the formula:

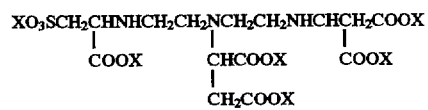

wherein X is independently selected from the group consisting of hydrogen, sodium, potassium, lithium, ammonium, monoethanolammonium, diethanolammonium, triethanolammonium and mixtures thereof.

17. A compound as defined in claim 16 wherein X is hydrogen.

18. A compound as defined in claim 16 wherein X is sodium.

19. A compound as defined in claim 16 wherein X is monoethanolamine.

20. A compound as defined in claim 16 wherein X is triethanolamine.

* * * * *